United States Patent [19]
Campbell et al.

[11] Patent Number: 6,139,572
[45] Date of Patent: *Oct. 31, 2000

[54] DELIVERY SYSTEM FOR INTRALUMINAL VASCULAR GRAFTS

[75] Inventors: Carey V. Campbell; Alvaro J. Laguna, both of Flagstaff, Ariz.

[73] Assignee: W. L. Gore & Associates, Inc., Newark, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/018,319

[22] Filed: Feb. 3, 1998

Related U.S. Application Data

[62] Division of application No. 08/529,694, Sep. 18, 1995, abandoned.

[51] Int. Cl.[7] ................................................ A61F 2/06
[52] U.S. Cl. ................................. 623/1.11; 623/1.1
[58] Field of Search ........................ 623/1, 1.11, 1.12, 623/1.2, 1.23, 1.25; 606/198, 108, 194, 192, 195

[56] References Cited

U.S. PATENT DOCUMENTS

| | | |
|---|---|---|
| 4,787,899 | 11/1988 | Lazarus . |
| 5,158,548 | 10/1992 | Lau et al. . |
| 5,207,695 | 5/1993 | Trout, III ................................ 606/153 |
| 5,219,355 | 6/1993 | Parodi et al. . |
| 5,290,295 | 3/1994 | Querals et al. . |
| 5,415,664 | 5/1995 | Pinchuk . |
| 5,453,090 | 9/1995 | Martinez et al. . |
| 5,480,423 | 1/1996 | Ravenscroft et al. . |
| 5,484,444 | 1/1996 | Braunschweiler et al. . |
| 5,522,883 | 6/1996 | Slater et al. . |
| 5,569,296 | 10/1996 | Marin et al. ............................. 606/198 |
| 5,599,307 | 2/1997 | Bacher et al. . |

FOREIGN PATENT DOCUMENTS

| | | |
|---|---|---|
| 646365 | 4/1995 | European Pat. Off. . |
| 9415549 | 7/1994 | WIPO . |
| 9618361 | 6/1996 | WIPO . |

*Primary Examiner*—Mickey Yu
*Assistant Examiner*—Alvin Stewart
*Attorney, Agent, or Firm*—Wayne D House

[57] ABSTRACT

A delivery system for use with intraluminal vascular grafts, allowing for easy delivery, deployment of an intraluminal graft and withdrawal of the delivery system. The system employs a balloon catheter to deploy one end of the graft and uses a separate means to deploy the remainder of the graft. A hollow, bullet-shaped tip is used to enclose the balloon during insertion and withdrawal of the delivery system, wherein the bullet-shaped tip is axially movable to either expose or enclose the balloon.

2 Claims, 6 Drawing Sheets

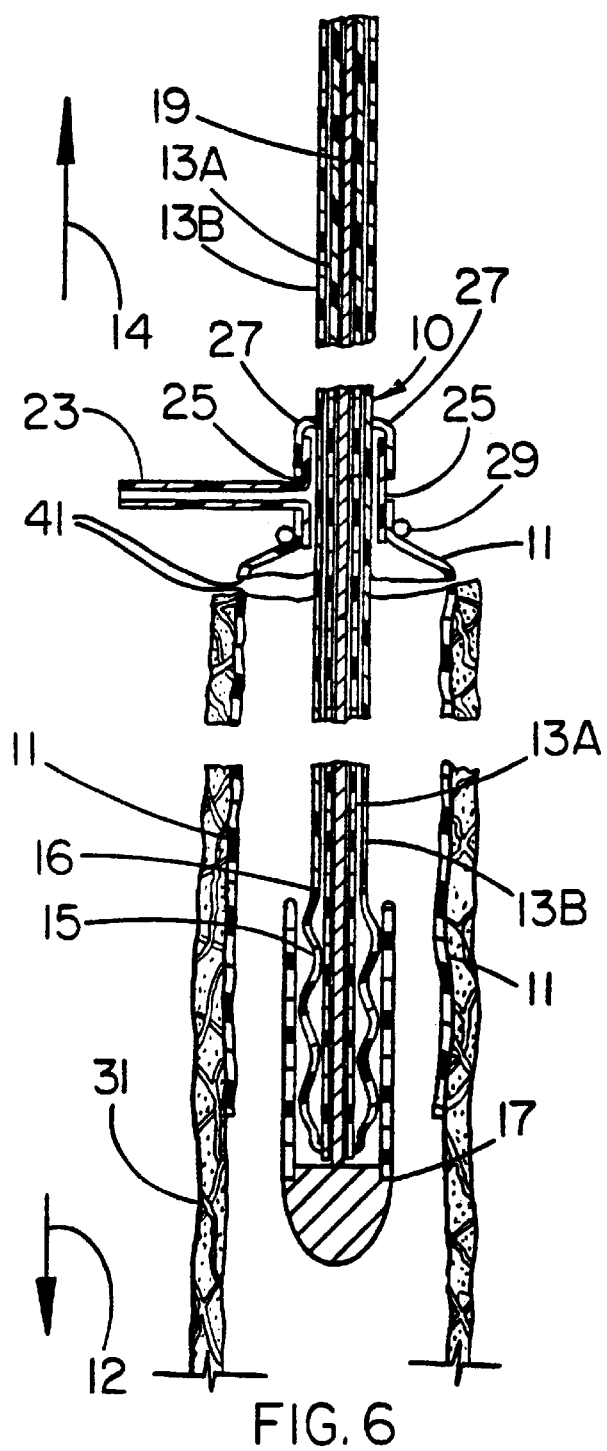
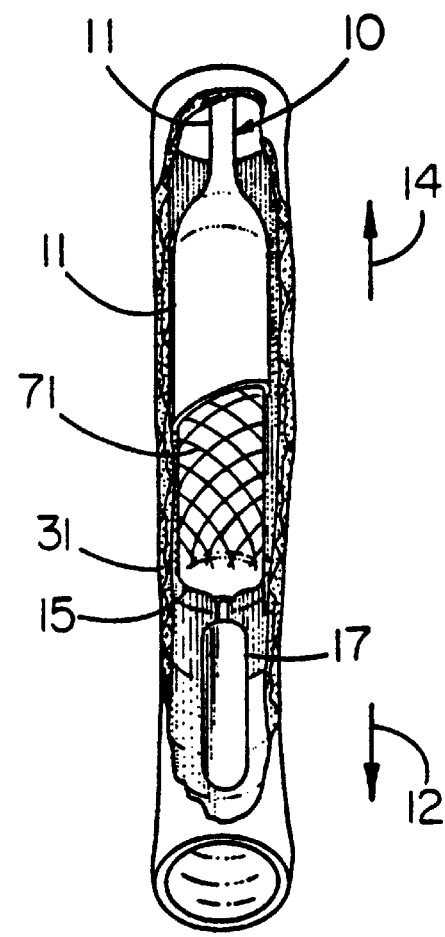
FIG. 6
FIG. 7

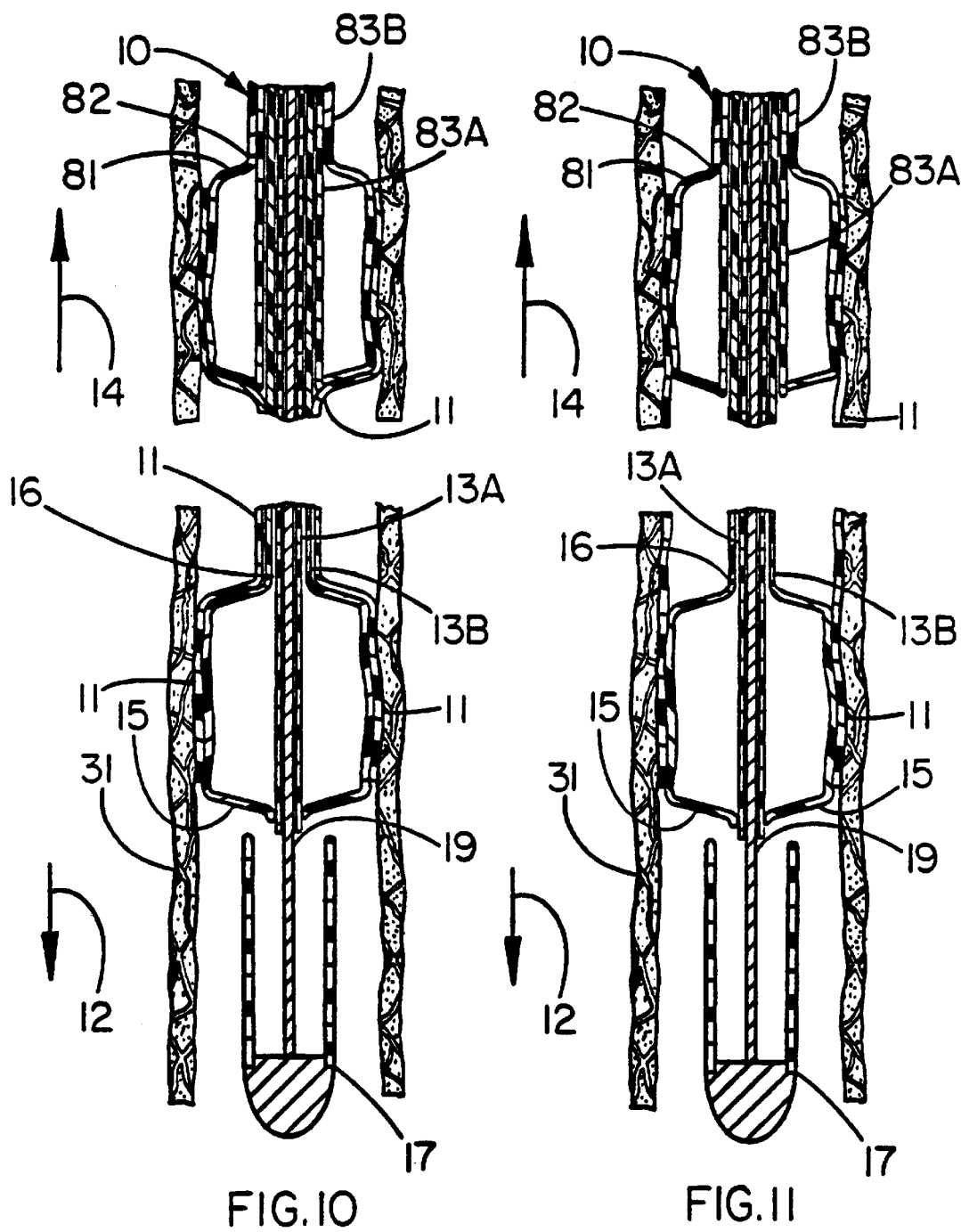

DELIVERY SYSTEM FOR INTRALUMINAL VASCULAR GRAFTS

CROSS REFERENCE TO RELATED APPLICATIONS

This application is a Division of application Ser. No. 08/529,694, filed Sep. 18, 1995 now abandoned.

FIELD OF INVENTION

This invention relates to the field of delivery systems useful for the delivery and implant of intraluminal vascular grafts.

BACKGROUND OF THE INVENTION

Intraluminal vascular grafts are fitted into the lumen of living blood vessels when it is desired to provide such a vessel with a new luminal surface for purposes of treating various vascular problems. These grafts are conventionally delivered using balloon catheters and guidewires. Once located as desired to provide the new vessel lining at the correct site, the intraluminal graft is deployed by inflation of the balloon portion of the balloon catheter to cause the intraluminal graft to deploy sufficiently to force it against the lumen of the living vessel, thereby providing the vessel with a new luminal surface. One shortcoming of this conventional method is due to the relatively short length of the balloons employed, requiring that the intraluminal graft be deployed in length segments by deflating the balloon after deploying a segment, moving the balloon to the next segment and reinflating the balloon.

This is done repeatedly until the entire length of the intraluminal graft has been adequately deployed. One or both ends of the intraluminal graft are secured to the blood vessel by the use of stents or by sutures. In some instances it may be acceptable to secure only the proximal end of the graft with either a stent, or sutures. A securing stent may be deployed simultaneously with balloon deployment of the end of the intraluminal graft, or alternatively the stent may be deployed subsequent to deployment of the intraluminal graft.

SUMMARY OF THE INVENTION

The present invention relates to an intraluminal delivery system for vascular grafts. An intraluminal vascular graft is defined herein as any vascular graft which is used to provide a new luminal surface for another conduit, with the new luminal surface located coaxially within that conduit. While the term conduits herein primarily describes living blood vessels, it is also intended to include other living body conduits. The term conduits is also considered to include prosthetic vascular grafts, stents including covered stents, and combinations thereof. The delivery system allows for simple and effective delivery of an intraluminal vascular graft to a desired location in the vascular system of a living body, and for deployment of the intraluminal graft as appropriate to fit the luminal surface of the conduit at the desired location. After deployment of the intraluminal graft, the delivery system is easily removed. The intraluminal graft may then be secured to the conduit by conventional surgical means such as by sutures. Alternatively, the system may be configured to include a stent located at one or both ends of the intraluminal graft with the stent placed coaxially between the balloon and the end of the intraluminal graft, whereby the stent and the end of the intraluminal graft are simultaneously deployed causing simultaneous deployment and attachment of the end of the intraluminal graft to the luminal surface of the conduit.

The system comprises a guidewire having a hollow, bullet-shaped distal end, a balloon catheter and separate inflation means for the balloon catheter and for deployment of an intraluminal graft. Deployment as used herein describes the process of causing an intraluminal graft to fit coaxially in close contact with the luminal surface of the conduit within which the graft has been placed, with little or no wrinkling of the intraluminal graft. Deployment may involve the circumferential distension of the graft or may involve unfolding of a graft previously folded into a compact volume for insertion. The hollow, bullet-shaped distal end encloses the balloon and the distal end of the intraluminal graft, allowing for easy insertion of the delivery system into the vascular system. The guidewire is located within a lumen of the catheter shaft of the balloon catheter to allow axial movement of the hollow, bullet-shaped end with respect to the balloon and the intraluminal graft. Balloon inflation means such as a syringe is fitted to the proximal end of the balloon catheter to accomplish inflation of the balloon located at the distal end. Separate inflation means such as a second syringe is provided for deployment of the intraluminal graft.

In use, the assembled system along with an intraluminal graft is introduced into the vascular system at a convenient site by conventional means such as a catheter introducer. The delivery system is inserted further into the vascular system until the desired location for the intraluminal graft is reached, which may be verified by conventional imaging techniques such as angiography in that portions of the system may be made to be radiopaque. Once properly located, the hollow, bullet-shaped tip is extended distally beyond the balloon by axial movement of the guidewire, after which the balloon is inflated causing deployment of the distal end of the intraluminal graft. The balloon is adequately inflated to cause the end of the intraluminal graft to be secured against the lumen of the conduit in which it is located and thereby sealed to the lumen. The intraluminal graft is then held captive between the balloon at the distal end and its attachment to a seal fitting located at the proximal end of the graft. The means for deploying the intraluminal graft is then activated, introducing a volume of an inflating medium, preferably a liquid such as saline into the interior of the tubular intraluminal graft between its ends adequate to cause deployment of the intraluminal graft, thereby bringing it into contact with the lumen of the living vessel. The pressure within both the balloon and the intraluminal graft is then released, leaving the intraluminal graft deployed outwardly against the lumen of the conduit. For a surgically transected conduit, the proximal end of the intraluminal graft is transected even with the transected end of the conduit. Again using the guidewire, the hollow, bullet-shaped end is moved in a proximal direction to enclose the deflated balloon, after which the delivery system is withdrawn leaving the intraluminal graft behind. The proximal end and optionally the distal end of the intraluminal graft are then secured using sutures if such an attachment is desired. Alternatively, the proximal end and optionally the distal end of the intraluminal graft may be secured using expandable stents, which offer the advantage of accomplishing attachment of the intraluminal graft via transluminal placement. An attaching stent may be deployed during inflation of the balloon portion of the delivery system, or alternatively may be separately deployed to attach the intraluminal graft subsequent to its delivery and deployment. According to either of the above attachment methods, it may be acceptable to leave the distal end of the intraluminal graft without attachment.

A primary advantage of the intraluminal graft delivery system of the present invention is that it does not require a protective tubular sheath to enclose the full length of the intraluminal graft during insertion. The use of such a sheath has multiple disadvantages. For example the presence of a sheath requires that the catheter shaft have adequate length to allow the sheath to be moved proximally for the equivalent of the full length of the intraluminal graft in order to free the length of the intraluminal graft for deployment. The presence of a sheath also increases the diameter of the delivery system for the full length of the intraluminal graft and thereby increases the bending resistance of the delivery system, causing it to be vulnerable to kinking and making it more difficult to navigate through tortuous pathways. The protective sheath can also be difficult to remove by sliding it proximally from over the intraluminal graft, which poses a risk of improper placement, or damage to the graft.

Still another advantage of the delivery system of the present invention is that it reduces the risk of back-filling of blood between the exterior surface of the intraluminal graft and the luminal surface of the conduit. The bullet-shaped tip also prevents the entry of blood into the lumen of the intraluminal graft until deployment is complete. Further, pressure may be applied to the balloon while it and the intraluminal graft are encased by the hollow tip, causing the intraluminal graft to be immobilized with respect to the tip and the balloon. This bullet-shaped tip may also be used advantageously with any angioplasty balloon catheter, whereby following inflation and deflation of such a catheter balloon, the tip may be moved proximally to enclose the balloon, thereby reducing its maximum transverse diameter to a minimum and consequently reducing the amount of drag caused by the balloon during subsequent withdrawal of the catheter. The tip may also be used as a deflation aid to an inflated balloon.

While the delivery system of the present invention is intended primarily for use within the vascular system of a living body, it is apparent that the system may be used within any body conduit which may be provided with a new lining. Further, the system and method of the present invention are also anticipated to be useful for providing a new interior surface lining to various pipes, tubes and vessels used in various mechanical or industrial applications.

BRIEF DESCRIPTION OF THE DRAWINGS

FIGS. 2–6 are longitudinal cross sections sequentially describing the delivery system of FIG. 1 during use.

FIG. 7 is a cut away perspective view of an alternative embodiment of the delivery system described by FIGS. 1–6 incorporating a stent between the balloon and the intraluminal vascular graft.

FIGS. 9–11 are longitudinal cross sections sequentially describing the delivery system of FIG. 8 during use.

DETAILED DESCRIPTION OF THE INVENTION

Figure 1:
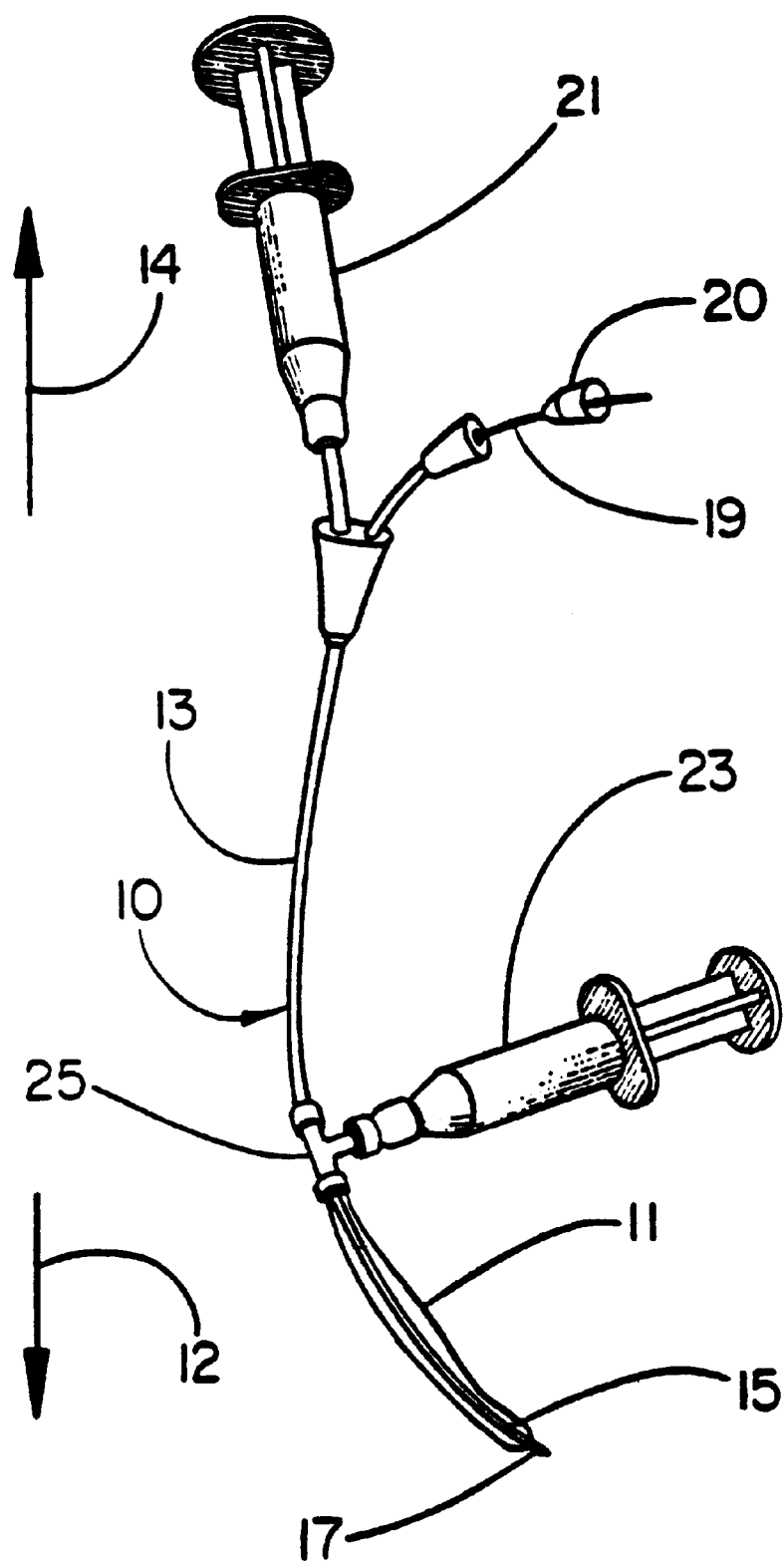
FIG. 1 is a perspective view of the delivery system of the present invention.

FIG. 1 is a perspective view of the delivery system 10 of the present invention while FIGS. 2–6 are sequential longitudinal cross sectional views of the inventive delivery system 10 in use within a body conduit 31. The delivery system 10 with its various components has a distal end 12 and a proximal end 14, as does the conduit 31 within which the delivery system is used. An intraluminal graft 11 is fitted coaxially over the distal end 12 of a balloon catheter 13. The balloon 15 is located within the distal end 12 of the intraluminal graft 11; both the balloon 15 and distal end 12 of the intraluminal graft 11 are enclosed within a hollow, bullet-shaped end 17 which is axially movable with respect to the balloon catheter 13 by a guidewire 19 connected to the hollow, bullet-shaped end 17. Guidewire 19 extends through guidewire lumen of the balloon catheter 13 within catheter shaft 13A and is operable by relative movement at the proximal end 14 of the balloon catheter 13 using the torquing device 20 as a handle.

Balloon 15 is connected via a second lumen of the balloon catheter 13 to a means for balloon inflation 21 such as the syringe shown by FIG. 1. This second lumen is preferably located coaxially around the first lumen. After the hollow, bullet-shaped end 17 has been moved axially by use of the guidewire 19 so as to no longer enclose the balloon, inflation of balloon 15 causes circumferential distension of the distal end 12 of intraluminal graft 11.

Proximal end 14 of intraluminal graft 11 is sealed to the exterior surface of balloon catheter 13 by seal fitting 25, which is in turn connected to a means for graft deployment 23 such as the syringe shown by FIG. 1.

Figure 2:
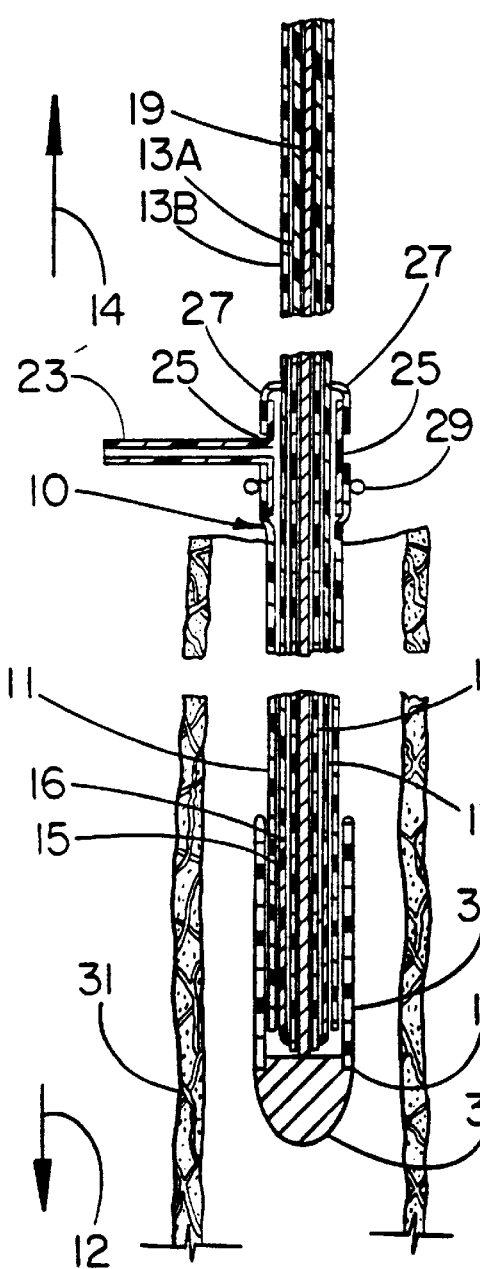
Figure 3:
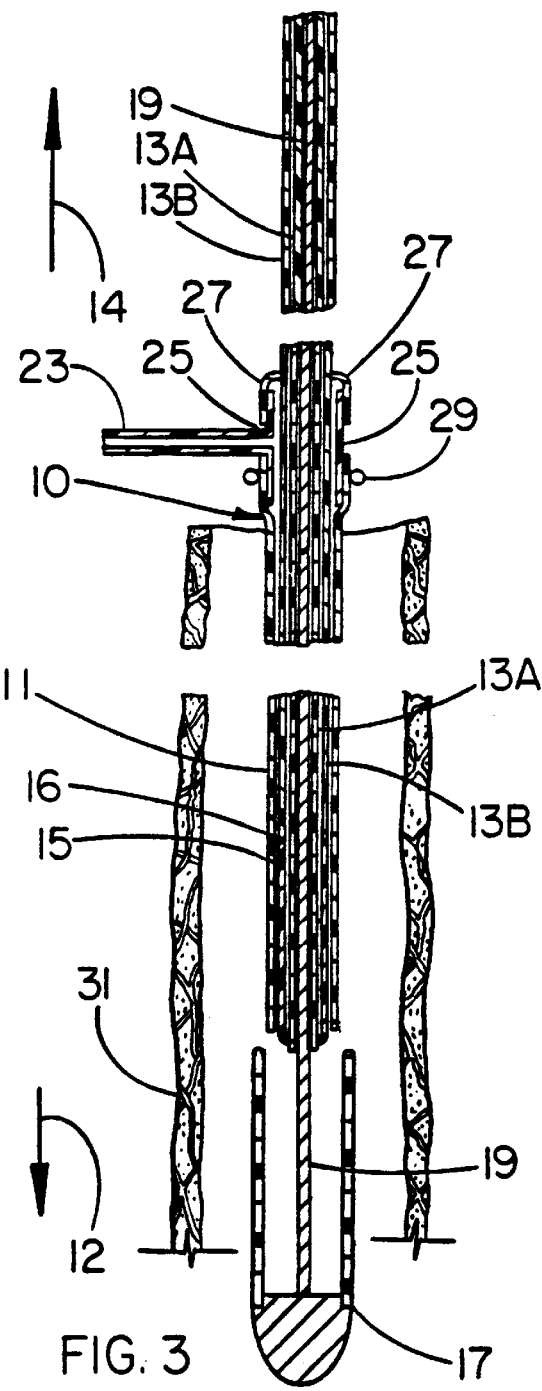

FIG. 2 describes in longitudinal cross section the initial configuration of delivery system 10 as it appears during insertion into a conduit 31 for delivery and deployment of intraluminal graft 11. The axial discontinuities in the cross section indicate that the lengths between the portions shown by the figures may be any length desired. In the case depicted, the proximal end 12 of conduit 31 has been surgically transected to provide access and to allow for attachment of intraluminal graft 11 to the proximal end 12 of conduit 31 by sutures, stent or other suitable means.

Balloon catheter 13 is provided with at least two lumens. The guidewire is contained within a separate guidewire lumen while a second lumen is provided to connect means for balloon inflation 21 with balloon 15. FIG. 2 depicts these lumens in coaxial relationship with the guidewire lumen enclosed by catheter shaft 13A and the lumen connecting balloon 15 and means for balloon inflation 21 enclosed by catheter shaft 13B. While a coaxial relationship is depicted, any geometric relationship may be used which provides the at least two lumens.

FIG. 2 and subsequent figures depict balloon 15 connected to the distal end 12 of catheter shaft 13B in end-to-end fashion at location 16. It is apparent that an alternative connection may be made by overlapping the proximal end of balloon 15 with catheter shaft 13B.

During insertion, balloon 15 is coaxially enclosed by hollow, bullet-shaped end 17 which is connected to and axially movable by guidewire 19. End 17 comprises a bullet-shaped tip 37 and tubular portion 39. While FIG. 2 describes that tip 37 is made of metal for easy visualization and tubular portion 39 is of a plastic which is preferably a lubricous plastic such as PTFE, it is apparent that end 17 may be made as a one-piece construction from a single material which may be radiopaque if desired.

Seal fitting 25 seals the proximal end 14 of the intraluminal graft 11 to the exterior surface of balloon catheter 13 and provides for connection to means for graft deployment 23. Seal fitting 25 includes sealing means 27 such as the seal shown by FIG. 2 and attaching means 29 such as the ring shown for sealingly connecting the proximal end 14 of intraluminal graft 11 to seal fitting 25. All sealing functions provided by seal fitting 25 must withstand the pressure from the means for graft deployment 23 during deployment of the intraluminal graft 11.

Figure 4:
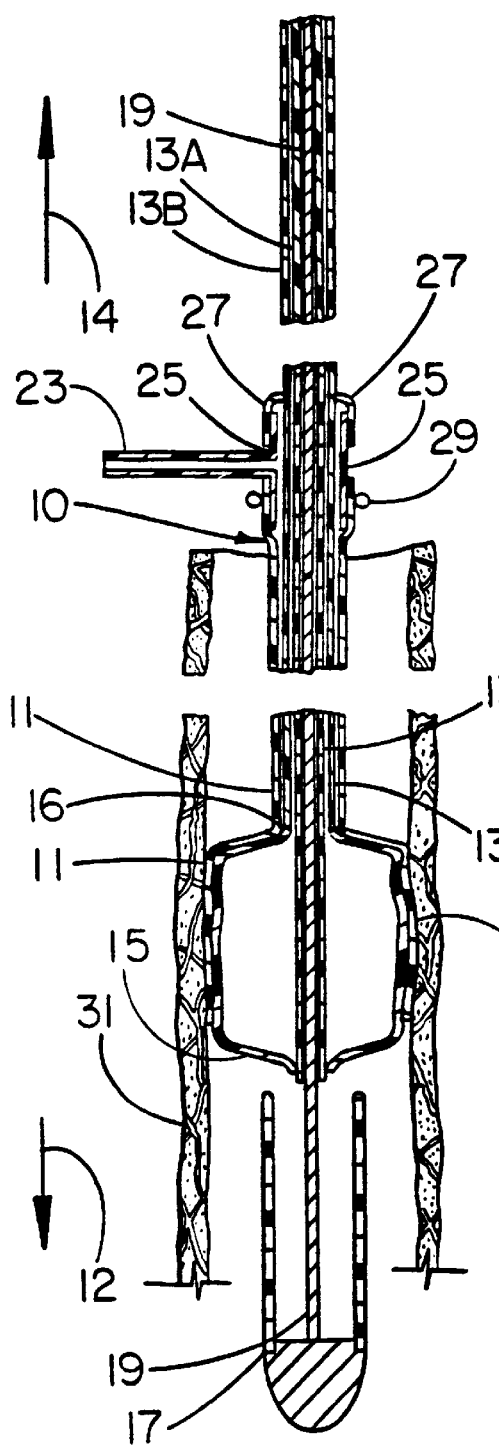
Figure 5:
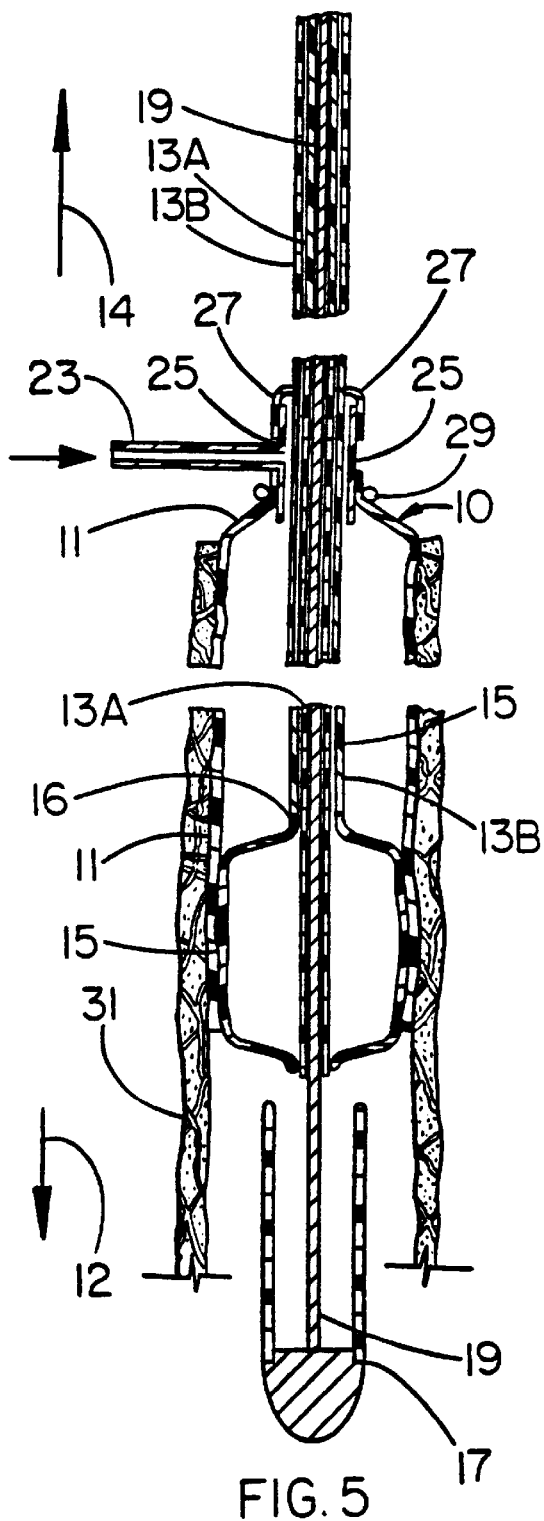

When located as desired, the hollow, bullet-shaped end 17 is moved axially in a distal direction 12 by guidewire 19 with activation of guidewire 19 provided at the proximal end 14 of balloon catheter 13. This is described by FIG. 3. After end 17 is clear of balloon 15, balloon 15 is inflated as shown by FIG. 4 by pressure from the means for balloon inflation 21. Inflation of balloon 15 is continued until balloon 15 has increased in diameter adequately to deploy the distal end 12 of intraluminal graft 11 enough to bring it into good contact with the lumen of conduit 31. This causes the distal end of the intraluminal graft 11 to become sealed against the luminal surface of conduit 31 which then allows pressure to be applied to the interior of the remainder of intraluminal graft 11 via means for graft distension 23. This pressure is applied until the intraluminal graft 11 is fully deployed along its length into contact with the lumen of conduit 31 as described by FIG. 5.

As shown by FIG. 6, once the intraluminal graft 11 has been fully deployed, the pressure applied to the interior of the balloon 15 is released by withdrawing the inflating medium or by sliding hollow tip 17 over the balloon 15, causing it to compact.

Proximal end 14 of intraluminal graft 11 is transected even with the previously transected proximal end 12 of conduit 31 as shown by edges 41, thus enabling subsequent attachment of the proximal end 14 of intraluminal graft 11 to conduit 31 by sutures, a stent or other suitable means.

Also as shown by FIG. 6, withdrawal of the delivery system 10 following deployment of intraluminal graft 11 is accomplished by axially moving hollow, bullet-shaped end 17 back over deflated balloon 15, thereby again enclosing balloon 15 and minimizing the diameter of the deflated balloon. Enclosing balloon 15 in such a manner with a tubular, lubricous cover as provided by end 17 allows for easy removal of delivery system 10 with minimum drag.

FIG. 7 describes a cutaway perspective view of the use of a balloon expandable stent in conjunction with the delivery system 10. The view shown is sequentially equivalent to the longitudinal cross sectional view of FIG. 4 which describes inflation of the balloon 15 and deployment of the distal end of the intraluminal graft 11. To create the delivery system shown by FIG. 7, stent 71 is fitted coaxially over balloon 15 and coaxially within the distal end 12 of intraluminal graft 11 prior to insertion of the delivery system 10 into the vascular system of a living body. The distal ends 12 of the stent 71 and the intraluminal graft 11 extend to the distal end of balloon 15, which is not apparent from the cutaway perspective view of FIG. 7. Following insertion to a desired location within the vascular system, inflation of balloon 15 results in simultaneous deployment of the distal end 12 of intraluminal graft 11 and stent 71, so that when the distal end 12 of intraluminal graft 11 has been deployed sufficiently to come into circumferential contact with the lumen of conduit 31, it is simultaneously attached thereto by the balloon-expanded stent 71.

While this procedure describes securing of the intraluminal graft by the use of balloon-expandable stents, it is apparent that other types of stents may be used, such as, for example, self-expanding stents.

FIGS. 8–11 describes an alternative embodiment wherein seal fitting 25 is replaced by a second balloon catheter 83 having a balloon 81 located at the proximal end of the intraluminal graft. The use of the additional balloon at the proximal end of the intraluminal graft allows the entire procedure to be accomplished transluminally without requiring a surgical cut-down and avoids surgical transection of the conduit being repaired. Balloon 81 is provided with its own separate means for inflation 85 at the proximal end 14 of the delivery system 10. Graft 11 is deployed via means for graft deployment 24 at the proximal end of the delivery system 10. Seal fitting 22 seals the proximal end of the intraluminal graft to the exterior surface of balloon catheter 83. Alternatively (not shown by the Figures) balloon 81 may be inflated simultaneously with balloon 15 using a common means for balloon inflation. Preferably, balloon catheter 83 is slidably coaxial with balloon catheter 13 whereby balloon 81 may be moved axially along balloon catheter 13 to allow the intraluminal graft 11 to be cut to any desired length and allow balloon 81 to be located at the proximal end of intraluminal graft 11 regardless of the length of that graft.

As described by FIGS. 8–11, catheter 83 is provided with an inner lumen which enables deployment of intraluminal graft 11 and is enclosed by catheter shaft 83A, and with an outer lumen which allows inflation of balloon 81, the outer lumen being enclosed by catheter shaft 83B.

Figure 8:
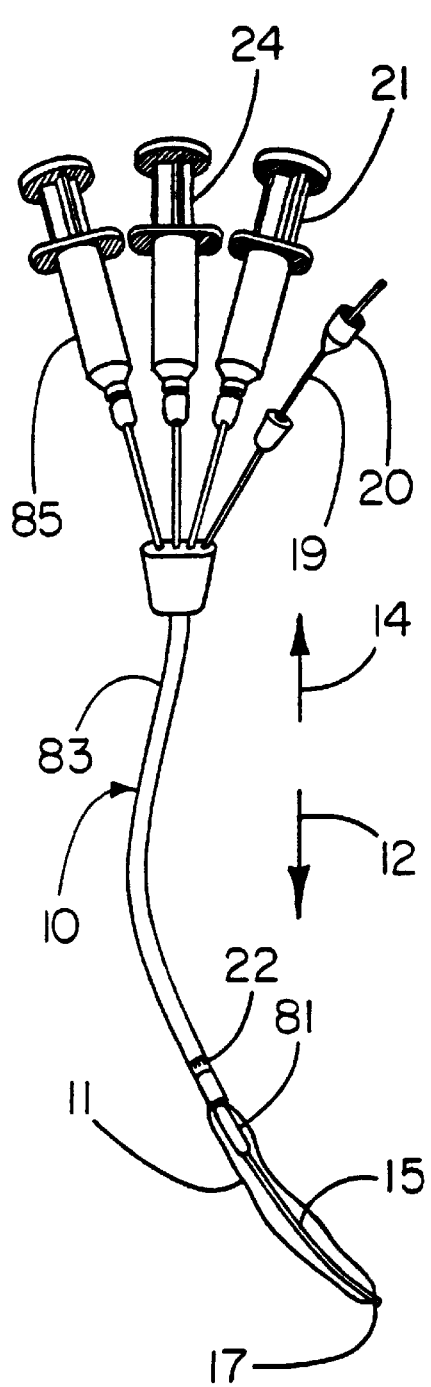
FIG. 8 is a perspective view of an alternative embodiment of the delivery system incorporating a balloon at each end of the intraluminal graft.

FIG. 8 and subsequent figures depict balloon 81 connected to the distal end 12 of catheter shaft 83B in end-to-end fashion at location 82. It is apparent that an alternative connection may be made by overlapping the proximal end of balloon 81 with catheter shaft 83B.

Figure 9:
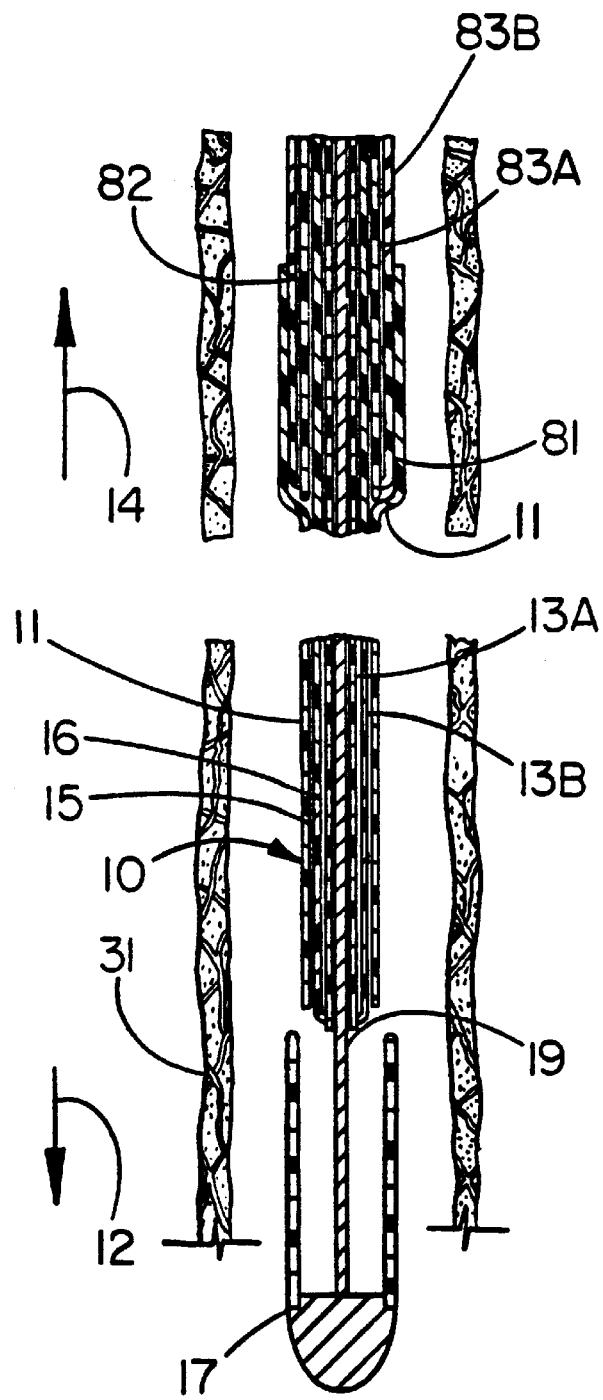

FIGS. 9, 10 and 11 are longitudinal cross sections sequentially describing the delivery system 10 of FIG. 8 during use. FIG. 9 describes this embodiment after insertion into a vascular system and after the bullet-shaped tip 17 has been extended distally by guidewire 19 beyond the end of balloon 15. Proximal end 14 of intraluminal graft 11 coaxially covers the second balloon 81. As shown by FIG. 10, the next step involves inflation of both balloons 15 and 81. Preferably balloon 15 at the distal end of the intraluminal graft 11 is inflated first, thereby securing that end of intraluminal graft 11 to the wall of the conduit 31. Second balloon 81 is then inflated, securing the proximal end 14 of intraluminal graft 11 to the wall of the conduit 31. Following inflation of both balloons 15 and 81 the portion of the intraluminal graft 11 between the distal and proximal ends previously secured by the balloons is deployed by activating means for graft deployment 24 as described by FIG. 11. After the entire length of the intraluminal graft 11 has been deployed against the wall of the conduit 31, balloons 15 and 81 are deflated, the bullet-shaped tip 17 is moved proximally back into place over balloon 15 and the entire delivery system 10 is withdrawn.

EXAMPLE

This example describes the construction of an embodiment of the present invention.

One end along the longitudinal axis of a female tee luer lock fitting (part number H-06359-47, supplied by Cole Parmer, Niles, Ill.) having a 4 mm inner diameter was fitted with a self sealing injection site (Injection Site with Luer Lock manufactured by Baxter Healthcare Corporation, Deerfield, Ill.). A hole was created through the injection site, and the balloon end of a model 12TL0806F Fogarty[7] Thru-Lumen Embolectomy Catheter manufactured by Baxter Healthcare Corporation (Irvine, Calif.) was passed through this hole, situating the female tee luer lock fitting with one uncovered end facing toward the distal end of the catheter, another uncovered end perpendicular to the catheter shaft, and the third end (fitted with the injection site) facing the proximal end of the catheter. The catheter was then fitted with a 0.64 mm diameter Ultra-Select Nitinol Guidewire manufactured by Microvena (White Bear Lake, Minn.). This guidewire was modified to the extent that the flexible end was removed, and a stainless steel bullet-shaped tip having a 3.2 mm outer diameter was welded onto the end of the wire. This bullet-shaped tip had a 0.76 mm diameter hole bored along its longitudinal axis, and was stepped at one end to an outer diameter of about 2.9 mm so that a 2.3 cm long piece of PTFE tubing having and inner diameter of 2.9 mm and an outer diameter of 3.2 mm could be pressed onto the stepped end of the bullet-shaped tip. This resulted in one end of the guidewire having a securely affixed bullet-shaped tip including a short hollow section. When the guidewire was fully inserted into its lumen in the embolectomy catheter, the hollow section of the bullet-shaped tip coaxially covered the balloon portion of the embolectomy catheter. The torquing device provided with the guidewire was placed on the wire approximately 3 cm away from the end of the threaded fitting attached to the proximal end of the catheter shaft. This placement of the torquing device enabled the device to be used to slide the guidewire and the attached bullet-shaped tip distally, such that the hollow section of the tip was no longer coaxially covering the balloon portion of the catheter.

At this point the delivery system was ready to have an intraluminal vascular graft installed onto it. The graft, having an inside diameter of 3 mm and a wall thickness of about 0.13 mm was slid over the bullet-shaped tip, coaxially fitting it over the catheter shaft. The torquing device was used to slide the guidewire and the attached bullet shaped tip distally, such that the hollow portion of the tip was no longer encasing the balloon portion of the catheter. The distal end of the graft was placed such that it coincided with the proximal edge of the distal radiopaque balloon marker band. The hollow portion of the bullet-shaped tip was then slid proximally, encasing both the most distal portion of the vascular graft as well as the balloon portion of the catheter.

The female tee luer lock fitting and attached injection site were then slid distally along the shaft of the catheter to the proximal end of the intraluminal graft, and this end of the intraluminal graft was then ligated onto the open end of the female tee luer lock fitting facing the balloon portion of the catheter. The delivery system, now fitted with an intraluminal graft, was ready for use.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A delivery system for intraluminal grafts comprising:
   a) a balloon catheter having a proximal end and a distal end and further having an inflatable balloon at the distal end and means for inflating the balloon, said means for inflating the balloon being located at or near the proximal end of the catheter, said balloon and means for inflating the balloon being connected by a first lumen extending therebetween, wherein said balloon may be inflated to deploy a first length portion of an intraluminal graft; and
   b) separate means for deploying a second length portion of the intraluminal graft;

wherein the balloon is located within the first length portion of the intraluminal graft and the separate means for deploying Is located entirely within the second length portion of the intraluminal graft displaced axially from the first length portion of the Intraluminal graft, and further wherein the separate means for deploying is not a balloon.

2. A delivery system for intraluminal grafts according to claim 1 wherein the means for inflating the balloon is a first syringe containing a liquid and wherein the separate means for deploying the second length portion of the intraluminal graft is a second syringe containing a liquid.

* * * * *